United States Patent [19]

Johnson et al.

[11] 4,008,139
[45] Feb. 15, 1977

[54] FLUORINATED COMPOUNDS

[75] Inventors: Joseph H. Johnson; Alvin S. Gordon, both of China Lake; William P. Norris, Ridgecrest, all of Calif.

[73] Assignee: The United States of America as represented by the Secretary of the Navy, Washington, D.C.

[22] Filed: Dec. 22, 1975

[21] Appl. No.: 643,271

[52] U.S. Cl. .................. 204/162 R; 260/632 R; 260/635 R
[51] Int. Cl.$^2$ .................. B01J 1/10; C07C 31/34
[58] Field of Search ............ 204/162 R; 260/632 R, 260/635 R

[56] References Cited
OTHER PUBLICATIONS

Gordon et al., International Journal of Chemical Kinetics, vol. VII, pp. 15 to 22 (1975).

Howard et al., J. Am. Chem. Soc., vol. 89, pp. 1422 to 1430 (1967).

*Primary Examiner*—Leland A. Sebastian
*Attorney, Agent, or Firm*—R. S. Sciascia; Roy Miller; L. E. K. Pohl

[57] ABSTRACT

1,1,4,4-Tetrakis(trifluoromethyl)butan-1,4-diol and 1,1-bis (trifluoromethyl)propanol-1 are prepared by reacting gaseous hexafluoroacetone and ethane in a transparent container in the presence of sunlight. The diol is a crystalline solid and the propanol-1 is a liquid. The diol is useful as a monomer in the field of polymer chemistry. That is, polymers such as polyurethans and polyesters which find many applications in the chemical industry can be made by reacting the proper material with the diol of this invention. The propanol-1 is useful as a plasticizer for polyurethans and other plastics.

5 Claims, No Drawings

FLUORINATED COMPOUNDS

BACKGROUND OF THE INVENTION

1. Field of the Invention.

This invention relates to the chemical compounds 1,1,4,4-tetrakis(trifluoromethyl)butan-1,4-diol and 1,1-bis(trifluoromethyl) propanol-1 and to methods for preparing them.

2. Description of the Prior Art.

α, ω Glycols have found considerable use in the chemical arts. For example, 1,4-butandiol, made by the hydrolysis of tetrahydrofuran or from a reaction between acetylene and formaldehyde, is used in the production of Perlon U (a polyurethan fiber) and in the production of γ-butyrolactone.

Heavily fluorinated organic compounds have also found considerable use. As examples, consider the fluorinated compounds well known as the freons and polytetrafluoroethylene (Teflon).

Accordingly, in experiments leading to this invention, it was an objective to prepare a multifunctional alcohol (α, ω glcyol) which could be used in the production of polyurethans and which was heavily fluorinated to take advantage of the oxidation resistant water repellant characteristics known to be imparted by fluorine. In preparing the multifunctional alcohol, a monofunctional alcohol, 1,1-bis(trifluoromethyl) propanol-1, was found to be a valuable side product. Insofar as is known by the inventors neither 1,1,4,4-tetrakis(trifluoromethyl) butan-1,4-diol nor 1,1-bis(trifluoromethyl)propanol-1 were ever prepared prior to the preparation described herein.

The most pertinant prior art known of by the inventors is an article entitled *The Free-Radical Chemistry of Fluoro Ketones. I. Reaction with Saturated Substrates*, E. G. Howard, P. B. Sargeant, and C. G. Krespan, J. Amer. Chem. Soc., 89, 1422 (1967). In this article, Howard et al describe the reaction of various materials with hexafluoroacetone. Among the materials reacted with hexafluoroacetone are n-butane and isobutane.

To react n-butane with hexafluoroacetone, Howard et al dissolved n-butane (a gas to room temperature) and hexafluoroacetone in $CFCl_2CF_2Cl$ and irradiated the solution with ultraviolet light from a mercury light. Their analysis showed that they had abtained some 2:1 hexafluoroacetone-n-butane adduct.

To react isobutane with hexafluoroacetone, Howard et al dissolved the two materials in $CFCl_2CF_2Cl$ and irradiated the solution with ultraviolet light from a mercury light in a manner similar to that used in the n-butane-hexafluoroacetone reaction except that irradiation was carried out for less time (2 days in the latter case as opposed to 5 days in the n-butane-hexafluoroacetone case). Their analysis indicated that perfluoropinacol and 1,1,1-trifluoromethyl-2-hydroxy-4-methyl-4-pentene were the major products obtained.

SUMMARY OF THE INVENTION

The heavily fluorinated α, ω glycol, 1,1,4,4-tetrakis (trifluoromethyl)butan-1,4-diol of this invention is prepared by reacting hexafluoroacetone and ethane (both gaseous materials at room temperature) in a transparent container in the presence of sunlight. A plurality of compounds are formed among which are the desired 1,1,4,4-tetrakis(trifluoromethyl)butan-1,4-diol and a monofunctional alcohol 1,1-bis(trifluoromethyl)-propanol-1 which has also been found to be useful.

DESCRIPTION OF THE PREFERRED EMBODIMENT

The preparation of 1,1-bis(trifluoromethylpropanol-1 and 1,1,4,4-tetrakis(trifluoromethyl)butan-1,4-diol may be most conveniently described by means of specific examples.

EXAMPLE 1

A 10 liter transparent Pyrex, round bottomed flask was evacuated to $10^{-3}$ mm pressure and then charged with 430 mm pressure ethane and 860 mm pressure of hexafluoroacetone (this is a 1:2 molar ratio of ethane to hexafluoroacetone). The reaction vessel was then exposed to 5 hours (0940–1440) directed sunlight (JUly, China Lake, California, temperature in the range of from 25° to 45° C) after which time the pressure in the reaction vessel was 658 mm. The next day the reaction vessel was exposed to direct sunlight for 6 hours (0900–1500) after which time the pressure in the reaction vessel was 359 mm. The reaction vessel, at 25° C, was evacuated to a pressure of 0.1 mm through a trap cooled with liquid nitrogen to give 42.5 g of liquid products leaving 41.7 g of solid residue in the reaction vessel.

Distillation of the liquid fraction at 705 mm pressure gave 31.0 g of 1,1-bis(trifluoromethyl)propanol-1, b.p. 75°–85° C. The infrared spectrum of this material is identical with that of 1,1-bis(trifluoromethyl) propanol-1 prepared by another route reported below.

The 41.7 g of solid residue was recrystallized twice from $CHCl_3$ to give 14.0 g of material, mp. 95°–97° C. Distillation of this material gave 11.0 g of 1,1,4,4-tetrakis(trifluoromethyl)butan-1,4-diol, mp. 96°–98° C, b.p. 155°–157° C/705 mm. Recrystallization of the distillate from chloroform raised the melting point to 97°–99° C.

Anal. Calcd. for $C_8H_6F_{12}O_2$: C, 26.53; H, 1.67; F, 62.96. Found: C, 26.20; H, 1.50; F, 62.15.

EXAMPLE 2

By starting the experiment with a 1:1 molar ratio of ethane to hexafluoroacetone, 47.3 g 1,1-bis(trifluoromethyl)propanol-1, b.p. 75°–80° C/705 mm. and 6.0 g of 1,1,4,4-tetrakis(trifluoromethyl) butan-1,4-diol, m.p. 96°–98° C, were obtained. From these data it will become apparent that increasing the molar ratio of ethane to hexafluoroacetone will increase the yield of the propanol-1 with respect to the diol. The converse is also true. That is, the more hexafluoroacetone one uses with respect to ethane, the more diol one will achieve with respect to the monofunctional alcohol. When an excess of ethane is used, i.e., when it is desired to form primarily 1,1-bis(trifluoromethyl) propanol-1, the amount of excess used is immaterial. That is, ten or even a hundred moles of ethane can be used for every mole of hexafluoroacetone with excellent results. On the other hand, it has been found that it is not advisable to use more than about twelve moles of hexafluoroacetone per mole of ethane if one wishes to have the diol as the predominant product. If a larger excess than this of the hexafluoroacetone is used, by-products begin to predominate and it becomes difficult to separate the diol from them.

EXAMPLE 3

1,1-Bis(trifluoromethyl)propanol-1 was prepared by a separate method.

Magnesium turnings, 6.1 g and 1 ml EtI were added to 25 ml ether in a round bottomed flask fitted with a condensor. The EtI initiated a Grignard reaction. After reaction began 100 ml ether was added and then 27.2 g EtBr was added dropwise to maintain reflux of ether. to form EtMgBr Grignard reagent. When the EtBr was all added, 41.5 g gaseous hexafluoroacetone was added to the stirred reaction mixture. Then 100 ml $H_2O$ and 25 ml conc. hydrochloric acid were added to the mixture to hydrolyze it. The ether phase was then separated and dried over $CaCl_2$ Ether was distilled off and a liquid fraction, b.p. 60°–90° C/705 mm, was collected. This fraction was shaken with 50 ml 30% fuming sulfuric acid. An organic phase separated containing dissolved $I_2$. The $I_2$ was removed by shaking with Hg followed by filtration. Distillation gave 7.0 g of 1,1-bis(trifluoromethyl) propanol-1, b.p. 75°–76° C/705 mm. Infrared absorption spectrum showed O-H bands at 2.75 and 2.85 $\mu$, C-H bands at 3.33, 3.38 and 3.45 $\mu$ and C-F bands at 8–9 $\mu$.

Anal. Calcd. for $C_5H_6F_6O$: C, 30.62; H, 3.09; F, 58.13. Found: C, 31.11; H, 3.21; F, 56146.

The reactions occurring in this example may be illustrated as follows:

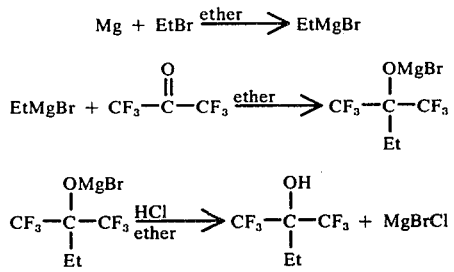

The diols of this invention readily react with diisocyanates such as hexamethylene diisocyanate to form polyurethans when the two monomers are mixed. Also, the diols of this invention readily react with acid halides and the like to form fluorinated polyesters. The polymers which are thus formed, being heavily fluorinated, are valuable because of their water resistance and their resistance to oxidation.

The monomfunctional alcohol of this invention may be used as a plasticizer for various polymers, including polyurethans, by mixing it into the polymeric material in any way usual to the art.

What is claimed is:
1. 1,1,4,4-Tetrakis(trifluoromethyl)butan-1,4-diol.
2. 1,1-Bis(trifloromethyl)propanol-1.
3. A method for preparing tetrakis(trifluoromethyl)butan-1,4-diol and 1,1-bis(trifluoromethyl)propanol-1 comprising the steps of:
   A. charging a transparent container with a mixture of gaseous ethane and hexafluoroacetone;
   B. exposing the container to sunlight whereby a solid fraction and a liquid fraction are achieved;
   C. separating 1,1-bis(trifluoromethyl)propanol-1 from the liquid fraction by distilliation; and
   D. separating 1,1,4,4-tetrakis(trifluoromethyl)butan-1,4-diol from the solid fraction by distillation.
4. A method according to claim 3 wherein the molar ratio of ethane to hexafluoroacetone is in the range of from 100:1 to 1:12.
5. A method for preparing 1,1-bis(trifluoromethyl)propanol-1 comprising the steps of:
   A. reacting hexafluoroacetone with ethyl magnesium bromide Grignard reagent in ether and hydrolyzing the material formed with HCl whereby 1,1-bis-(trifluoromethyl)propanol-1 is formed; and
   B. separating the 1,1-bis(trifluoromethyl)propanol-1 from the ether by distillation.

* * * * *